(12) United States Patent
Mullen et al.

(10) Patent No.: US 9,283,192 B2
(45) Date of Patent: Mar. 15, 2016

(54) DELAYED PROLONGED DRUG DELIVERY

(75) Inventors: Alexander Mullen, Glasgow (GB); Howard Stevens, Glasgow (GB); Sarah Eccleston, Scotstoun (GB)

(73) Assignee: UNIVERSITY OF STRATHCLYDE, Glasgow (GB)

( * ) Notice: Subject to any disclaimer, the term of this patent is extended or adjusted under 35 U.S.C. 154(b) by 0 days.

(21) Appl. No.: 13/582,926

(22) PCT Filed: Mar. 4, 2011

(86) PCT No.: PCT/GB2011/000307
§ 371 (c)(1),
(2), (4) Date: Oct. 2, 2012

(87) PCT Pub. No.: WO2011/107750
PCT Pub. Date: Sep. 9, 2011

(65) Prior Publication Data
US 2013/0022677 A1    Jan. 24, 2013

(30) Foreign Application Priority Data
Mar. 5, 2010   (GB) .................................. 1003734.9

(51) Int. Cl.
*A61K 9/20* (2006.01)
*A61K 9/22* (2006.01)
*A61K 9/24* (2006.01)

(52) U.S. Cl.
CPC ............... *A61K 9/209* (2013.01); *A61K 9/2013* (2013.01); *A61K 9/2054* (2013.01)

(58) Field of Classification Search
None
See application file for complete search history.

(56) References Cited

U.S. PATENT DOCUMENTS

| | | | |
|---|---|---|---|
| 4,832,958 A | 5/1989 | Baudier et al. | |
| 4,871,549 A | 10/1989 | Ueda et al. | |
| 5,145,644 A | 9/1992 | Park et al. | |
| 5,508,044 A | 4/1996 | Buxton et al. | |
| 5,558,879 A | 9/1996 | Chen et al. | |
| 5,614,220 A | 3/1997 | Hirakawa et al. | |
| 5,788,987 A | 8/1998 | Busetti et al. | |
| 6,312,724 B1 | 11/2001 | Odidi et al. | |
| 6,610,323 B1 | 8/2003 | Lundberg et al. | |
| 6,632,451 B2 | 10/2003 | Penhasi et al. | |
| 6,740,339 B1 | 5/2004 | Ohkouchi et al. | |
| 8,168,218 B2 | 5/2012 | Vergnault et al. | |
| 2004/0062804 A1* | 4/2004 | Lee et al. ....................... | 424/471 |
| 2004/0241100 A1 | 12/2004 | Kramer et al. | |
| 2005/0152974 A1 | 7/2005 | Boehm et al. | |
| 2005/0220877 A1 | 10/2005 | Patel et al. | |
| 2006/0177506 A1* | 8/2006 | Yanai et al. ................... | 424/468 |
| 2006/0257482 A1 | 11/2006 | Kumar et al. | |
| 2007/0098788 A1 | 5/2007 | Gore et al. | |
| 2009/0053308 A1 | 2/2009 | Ishida et al. | |
| 2009/0155358 A1 | 6/2009 | Diaz et al. | |
| 2009/0297601 A1 | 12/2009 | Vergnault et al. | |
| 2010/0040557 A1 | 2/2010 | Ke et al. | |
| 2013/0017262 A1 | 1/2013 | Mullen et al. | |
| 2013/0022676 A1 | 1/2013 | Mullen et al. | |

FOREIGN PATENT DOCUMENTS

| | | |
|---|---|---|
| EP | 0 546 593 A1 | 6/1993 |
| EP | 1 064 937 | 1/2001 |
| EP | 1 607 092 A1 | 12/2005 |
| EP | 2 098 250 A1 | 9/2009 |
| JP | H05-194188 A | 8/1993 |
| JP | 2001-515854 A | 9/2001 |
| JP | 2001-322927 A | 11/2001 |
| JP | 2003-503340 A | 1/2003 |
| JP | 2004-300148 A | 10/2004 |
| JP | 2005-508326 A | 3/2005 |
| JP | 2005-508327 A | 3/2005 |
| JP | 2005-508328 A | 3/2005 |
| JP | 2005-510477 A | 4/2005 |
| JP | 2008-517970 A | 5/2008 |
| JP | 2009-514989 | 4/2009 |
| WO | WO 99/12524 A1 | 3/1999 |
| WO | WO 01/00181 A2 | 1/2001 |
| WO | WO 03/026615 A2 | 4/2003 |
| WO | WO 03/026625 A1 | 4/2003 |
| WO | WO 03/026626 A2 | 4/2003 |
| WO | WO 03/030920 A1 | 4/2003 |
| WO | WO 2006/045618 A1 | 5/2006 |
| WO | WO 2008/079102 A1 | 7/2008 |
| WO | WO 2008/081891 A1 | 7/2008 |

(Continued)

OTHER PUBLICATIONS

Ghimire et al., "In-vitro/In-vivo Correlation of Pulsatile Drug Release from Press-Coated Tablet Formulations: A Pharmacoscintigraphic Study in the Beagle Dog", European Journal of Pharmaceutics and Biopharmaceutics, 2007, vol. 67, pp. 515-523.*

Ghimire, M. et al. "In-vitro/In-vivo Correlation of Pulsatile Drug Release from Press-Coated Tablet Formulations: A Pharmacoscintigraphic Study in the Beagle Dog," European Journal of Pharmaceutics and Biopharmaceutics, 2007, vol. 67, No. 2, 515-523.

Written Opinion of the International Searching Authority (Form PCT/ISA/237) mailed Mar. 12, 2012, for International Application No. PCT/GB2011/000307, 14 pages.

(Continued)

*Primary Examiner* — Michael B Pallay
(74) *Attorney, Agent, or Firm* — Hoxie & Associates LLC

(57) ABSTRACT

In one aspect, the present invention is concerned with a treatment where it is desired that an active agent is designed to be released in a prolonged manner at a time point some time after administration of the active agent. The present invention is particularly suited to administering an agent which may be released whilst a subject is sleeping, shortly before waking and continues to administer the drug during the early waking hours. As well as treating certain conditions by a particular regime, the invention also provides novel formulations for a delayed, followed by a prolonged release of drug.

24 Claims, 5 Drawing Sheets

(56) References Cited

FOREIGN PATENT DOCUMENTS

| WO | WO 2008/129517 A2 | 10/2008 |
| WO | WO 2009/154810 A2 | 12/2009 |

OTHER PUBLICATIONS

Stevens, H.N.E., "Chronopharmaceutical Drug Delivery," Journal of Pharmacy and Pharmacology, 1998, 50 (Supplement 9), 5.

Written Opinion of the International Searching Authority (Form PCT/ISA/237) mailed Mar. 12, 2012, for International Application No. PCT/GB2011/000306, 15 pages.

Written Opinion of the International Searching Authority (Form PCT/ISA/237) mailed Mar. 12, 2012, for International Application No. PCT/GB2011/000314, 14 pages.

Rowe, R. et al., Eds., Handbook of Pharmaceutical Excipients, Sixth Edition, Pharmaceutical Press, London, 2009, pp. 317-324.

Alvarez-Lorenzo, C. et al., "Evaluation of Low-substituted Hydroxypropylceulluloses (LHPCs) as Filler-Binders for Direct Compression." International Journal of Pharmaceutics, 2000, 197, 107-116.

English-language abstract of JP 2001-322927, Date of publication of application Nov. 20, 2001, 1 page.

English-language machine translation of JP 2001-322927, retrieved from the Japanese Patent Office website on May 2, 2015, 15 pages.

Fukui, E. et al., "Studies on Applicability of Press-coated Tablets Using Hydroxypropylcellulose (HPC) in the Outer Shell for Timed-release Preparations," Journal of Controlled Release, 2000, 68, 215-223.

Kleinebudde, P., "Application of Low Substituted Hydroxypropycellulose (L-HPC) in the Production of Pellets Using Extrusion / Spheronization" International Journal of Pharmaceutics, 96, pp. 119-128, (1993).

Shin-Etsu Guide on Low Substituted Hydroxypropyl Cellulose NF, cited in U.S. Appl. No. 13/582,913 in which Examiner listed publication date as 2008.

\* cited by examiner

DELAYED PROLONGED DRUG DELIVERY

CROSS REFERENCE TO RELATED APPLICATIONS

This application is a U.S. application under 35 U.S.C. 371 claiming benefit of PCT application No. PCT/GB2012/000307, filed on Mar. 4, 2011, which claims the benefit of GB application No. 1003734.9, filed on Mar. 5, 2010, the contents of each of which are incorporated herein by reference.

FIELD OF INVENTION

In one aspect, the present invention is concerned with a treatment where it is desired that an active agent is designed to be released in a prolonged manner at a time point some time after administration of the active agent. The present invention is particularly suited to administering an agent which may be released whilst a subject is sleeping, shortly before waking and continues to administer the drug during the early waking hours. As well as treating certain conditions by a particular regime, the invention also provides novel formulations for a delayed, followed by a prolonged release of drug.

BACKGROUND TO THE INVENTION

Time-dependent release mechanisms of drugs have been described in the literature for tablet, pellet and capsule formulation utilising a wide range of physicochemical and physicomechanical strategies. The common feature of all such formulations is that they are activated by contact with fluids following ingestion by the patient and the drug will be released at the predetermined time after administration. Only after the formulations come into contact with gastric fluids does the 'clock' start. Drug release subsequently takes place at a predicted time, although it will be appreciated that since the dosage unit will be travelling through the GI tract during the lag period, drug release will necessarily be at some unknown GI tract site. Using such formulation strategies, it will be possible to design delivery systems capable of releasing drugs according to chronotherapeutic principles and targeting release to the circadian rhythm of disease states (Stevens H N E, Chronopharmaceutical Drug Delivery. J Pharm Pharmac., 50 (s) 5 (1998)).

However, many of the formulations in the art rely on complex structures which can add to the cost of the manufacture of the drug and/or can be subject to malfunction leading to incorrect/inappropriate administration of the drug.

Delayed prolonged release formulations of verapamil, such as COVERA-HS® are known in the art. COVERA-HS® is a formulation designed to initiate release of verapamil 4-5 hours after ingestion. The delay in release is due to a layer between the active drug core and an outer semi-permeable membrane. However, the formulation is complex in its construction, requiring precision drilled holes in the outer membrane being formed.

Other tablet formulations have been described for pulsed release of verapamil, where a delay in release is effected by way of an outer hydroxypropylmethyl cellulose coating. There is the proposal to use such formulations in a chronotherapeutic manner.

Further verapamil formulations are described in U.S. Pat. No. 4,832,958, for example, although there is no teaching of formulations which show a delay in verapamil release.

It is amongst the objects of the present invention to obviate and/or mitigate at least one of the aforementioned disadvantages.

It is amongst the objects of the present invention to provide a formulation which may be easily and/or cheaply manufactured and which allows for an active agent to be administered in a prolonged manner, following a period of delay following administration.

SUMMARY OF INVENTION

The present inventors recognised a need to be able to administer, for example, a pharmaceutically active agent to a subject in a manner such that a delayed release of the pharmaceutically active ingredient could be achieved, followed by a prolonged delivery of the agent. Although this may have been possible using prior device/methods known in the art, many such devices/methods do not result in a desired physicochemical and/or physicomechanical profile and many are highly complex. As such there is therefore a distinct advantage in providing a simpler press-coated tablet formulation and method of treatment.

One particularly preferred embodiment relates to treating subjects who suffer from cardiovascular conditions. In a preferred embodiment therefore, the formulations of the present invention are for treating cardiovascular conditions such as hypertension, angina pectoris, cardiac failure, pulmonary hypertension, the primary or secondary prevention of cardiovascular disease, peripheral vascular disease, stroke, oedema, arrhythmias. Such formulations therefore comprise a pharmaceutically active agent for treating such cardiovascular conditions. For example this may be a calcium channel blocker, such as verapamil.

Thus, in a first aspect, the present invention provides a cardiovascular agent such as verapamil, formulated as a component of a press-coated tablet for treating a cardiovascular condition, wherein the formulation is intended to be administered immediately prior to a subject going to sleep (i.e. when a subject goes to bed at night for a prolonged period of sleep, such as 6-10 hours and hence is distinguished over shorter sleeping periods) and wherein the cardiovascular agent is substantially (such as less than 10%, 5% or even 1%) not released from the formulation for a period between 2-8 hours, such as 3-6 hours after administration of the formulation to the subject and thereafter the agent is released from the formulation in a prolonged manner such that the agent within the formulation is released continuously over a period of up to 2-8 hours, such as 3-6 hours.

In a further aspect there is provided a method of treating a cardiovascular condition, the method comprising administering a press-coated tablet comprising a cardiovascular agent, such as a verapamil to a subject, immediately before the subject intends sleeping, wherein the formulation substantially delays release of the drug for 2-8 hours, such as 3-6 hours following administration of the formulation and thereafter the drug is released continuously over a period of up to 2-8 hours, such as 3-6 hours.

Typically delayed release of the active agent is achieved by providing a press-coated tablet comprising a delayed release layer surrounding a core comprising the active agent. The delayed release layer may comprise a wax and a low-substituted hydroxypropyl cellulose (L-HPC), such as LH-32. The prolonged release of the active agent may be achieved by providing a core in which the active agent is admixed with a wax such as beeswax, carnuba wax, microcrystalline wax, hydrogenated castor oil. A particularly preferred wax is a glyceryl ester, such as glycerol behenate.

In a further aspect, the present invention provides a press-coated tablet formulation for a delayed, followed by a prolonged release of an active agent, the tablet comprising (a) a core comprising the active agent together with a wax and optionally one or more fillers; and
(b) a delayed release layer surrounding the core and comprising a wax and LH-32 in a ratio of 20:80 to 50:50 w/w; wherein the delayed release layer substantially delays release of the active agent within the core for between 2-8 hours, such as 3-6 hours after administration of the tablet by a subject and thereafter a prolonged release of the active agent from the core occurs, such that the active agent in the core is continuously released over a period of up to 2-8 hours, such as 3-6 hours.

The press coated tablets of the present invention, may further comprise:

(c) a top-coating layer comprising an active agent together with one or more excipients wherein a substantially immediate pulsed release of the active agent occurs following administration to the subject of the tablet.

By "immediately" is understood to mean that at least 70-90%, such as 80% of the active agent in the top layer or portion of the prerss-coated tablet, which is formulated for immediate release, is released within about 5-45 mins, such as 10-30 mins following administration.

The active agents of the above aspect include any active agent for which delayed followed by prolonged release is desirable. In a preferred embodiment of the invention, the active agent is a pharmaceutically acceptable active agent and includes pharmaceutical and veterinary active agents (often referred to as drugs). In other embodiments, the active agent includes agrichemical agents (such as fertilizers, herbicides, pesticides and fungicides), active agent used in the exterminating industry (such as toxins and poisons), and active agents used in industrial manufacturing (such as catalysts or catalytic quenchers).

The press-coated tablets of the present invention may be used to treat one or more of the following conditions/disorders or diseases:

Central Nervous System disorders, e.g. Neurogenic pain, stroke, dementia, Alzheimer's disease, Parkinson's disease, neuronal degeneration, meningitis, spinal cord injury, cerebral vasospasm, amyotrophic lateral sclerosis Cardiovascular disease, hypertension, atherosclerosis, angina, arterial obstruction, peripheral arterial disease, myocardial pathology, Arrhythmia, Acute Myocardial Infarction, Angina, Cardiomyopathy, Congestive heart failure, Coronary artery disease (CAD), Carotid artery disease, Endocarditis, Hypercholesterolemia, hyperlipidemia, Peripheral artery disease (PAD)

Genitourinary Disorders; erectile dysfunction, urinary organ diseases benign prostatic hypertrophy (BPH), Renal tubular acidosis, diabetic nephropathy, glomerulonephritis, glomerulosclerosis, urinary tract infection, faecal incontinence Ocular disease glaucoma, blephartitis, ocular hypertension, retinopathy, conjunctivitis, scleritis, retinitis, keratitis, corneal ulcer, iritis, Chorioretinal inflammation, macular edema, Xerophthalmia Pulmonary disease asthma, pulmonary hypertension, acute respiratory distress syndrome, COPD, emphysema, pneumonia, tuberculosis, bronchitis, Acute Bronchitis, Bronchiectasis, Bronchiolitis, Bronchopulmonary Dysplasia, Byssinosis, Coccidioidomycosis (Cocci), Cystic Fibrosis, Influenza, Lung Cancer, Mesothelioma Metabolic diseases; Hypercalciuria, Hyperglycemia, Hyperinsulinemic hypoglycemia, Hyperinsulinism, Hyperlysinuria, Hypoglycemia Exocrine and Endocrine; Addison's disease, Hypoaldosteronism, cushing's syndrome, diabetes, Goitre, Hyperthyroidism, Hypothyroidism, Thyroiditis, pancreatitis Hepatic disorders, Hepatitis, Non-alcoholic fatty liver disease, cirrhosis, hepatic cancer, Primary sclerosing cholangitis, primary biliary cirrhosis, Budd-Chiari syndrome, Autoimmune and Inflammatory diseases, multiple sclerosis rheumatoid arthritis, psoriasis, diabetes, sarcoidosis, Addison's Disease, Alopecia greata, Amyotrophic Lateral Sclerosis, Ankylosing Spondylitis, polyarticular Arthritis, Atopic allergy, topic Dermatitis, Autoimmune hepatitis, Celiac disease, Chagas disease, Coeliac Disease, Cogan syndrome, Crohns Disease, Cushing's Syndrome, Diabetes mellitus type 1, Endometriosis, Eosinophilic fasciitis, Fibromyalgia/Fibromyositis, Gastritis, Glomerulonephritis, Graves' disease. Guillain-Barré syndrome (GBS), Hashimoto's encephalitis, Hashimoto's thyroiditis, Haemolytic anaemia, Idiopathic Inflammatory Demyelinating Diseases, Idiopathic pulmonary fibrosis, interstitial cystitis, Juvenile idiopathic arthritis, Juvenile rheumatoid arthritis, Kawasaki's Disease, Lichen sclerosus, Lupus erythematosus, Ménière's disease, Myasthenia gravis, myositis, Narcolepsy, Pernicious anaemia, Perivenous encephalomyelitis, Polymyalgia rheumatica, Primary biliary cirrhosis, Psoriatic Arthritis, Reiter's syndrome, Rheumatoid fever, Sarcoidosis, Schizophrenia, Sjögren's syndrome, Spondyloarthropathy, Ulcerative Colitis Musculoskeletal disorders: osteoarthritis, osteoporosis, Osteonecrosis, Arthritis, Paget's Disease Bursitis, Costochondritis, Tendonitis Skin disorders; Acne, alopecia, candidiasis, celluliltis, dermatitis, eczema, epidermolysis bullosa, erythrasma, herpes, erysipelas, Folliculitis, impetigo, ringworm, scabies, Tinea, Trichomycosis ENT disorders; Otitis, sinusitis, laryngitis, pharyngitis, laryngitis, meniere's disease, labyrinthitis, Others: acute and chronic pain, viral infection, cancer, laryngitis, mastoiditis, myringitis, otitis media, rhinitis, sinusitis, Sialadenitis, Retropharyngeal Abscess, Tonsillopharyngitis, Gastro-intestinal Disorders Irritable bowel syndrome (IBS) necrotizing entercolitis (NEC) non-ulcer dyspepsia, chronic intestinal pseudo-obstruction, functional dyspepsia, colonic pseudo-obstructioduodenogastric reflux, gastroesophageal reflux disease, ileus inflammation, gastroparesis, heartburn, constipation—(e.g. constipation associated with use for medications such as opioids), colorectal cancer, colonic polyps, diverticulitis, colorectal cancer, Barretts Esophagus, Bleeding in the Digestive Tract, Celiac Disease, Colon Polyps, Constipation, Crohns Disease, Cyclic Vomiting Syndrome, Delayed Gastric Emptying (Gastroparesis), Diarrhea, Diverticulosis, Duodenal Ulcers, Fecal Incontinence, Gallstones, Gas in the Digestive Tract, Gastritis, Gastroesophageal Reflux Disease (GERD), Heartburn, Hiatal Hernia, Hemochromatosis, Hemorrhoids, Hiatal Hernia, Hirschsprung's Disease, Indigestion, Inguinal Hernia, Lactose Intolerance, Peptic Ulcers, Polyps, Porphyria, Primary Biliary Cirrhosis, Primary Sclerosing Cholangitis, Proctitis, Rapid Gastric Emptying, Short Bowel Syndrome, Stomach Ulcers, Ulcerative Colitis, Ulcers, Whipples Disease.

Exemplary active agents for use in the pharmaceutical and veterinary applications of the invention include analgesics, anaesthetics, anticonvulsants, antidiabetic agents, antihistamines, anti-infectives, antineoplastics, antiparkinsonian agents, antirheumatic agents, appetite stimulants, appetite suppressants, blood modifiers, bone metabolism modifiers, cardiovascular agents, central nervous system depressants, central nervous system stimulants, decongestants, dopamine receptor agonists, electrolytes, gastrointestinal agents, immunomodulators, muscle relaxants, narcotics, parasympathomimetics, sympathomimetics, sedatives, and hypnotics.

Said active agent or agents may be selected from the following:

Gastro Drugs

Antacids—aluminium hydroxide, magnesium carbonate, magnesium trisilicate, hydrotalcite, simeticonealginates, Antispasmodics—atropine sulphate, dicycloverine hydrochloride, hyoscine butylbromine, propantheline bromide, alverine citrate, mebeverine hydrochloride, Motility stimulants—metoclorpramide, domperidone H2-Receptor antagonists—Cimetidine, famotidinenizatidine, ranitidine Antimuscarinics—pirenzepine Chelates—Tripotassium dicitratbismuthate, sucralfate, Prostaglandin analogues—misoprostol Aminosalicylates—balsazide sodium, mesalazine, olsalazine, sulphasalazine Corticosteroids—beclometasone dipropionate, budenoside, hydrocortisone, prednisolone, Affecting immune response—ciclosporin, mercaptopurine, methotrexate, adalimumab, infliximab Stimulant Laxatives—bisacodyl, dantron, docusate, sodium picosulfate, Drugs affecting biliary composition and flow—ursodeoxycholic acid Bile acids sequestrants colestyramine, Oxyphencyclimine, Camylofin, Mebeverine, Trimebutine, Rociverine, Dicycloverine, Dihexyverine, Difemerine, Piperidolate Benzilone, Mepenzolate, Pipenzolate, Glycopyrronium, Oxyphenonium, Penthienate, Methantheline, Propantheline, Otilonium bromide, Tridihexethyl, Isopropamide, Hexocyclium, Poldine, Bevonium, Diphemanil, Tiemonium iodide, Prifinium bromide, Timepidium bromide, Fenpiverinium Papaverine, Drotaverine, Moxaverine 5-HT3 antagonists (Alosetron, Cilansetron), 5-HT4 agonists (Mosapride, Prucalopride, Tegaserod) Fenpiprane, Diisopromine, Chlorbenzoxamine, Pinaverium, Fenoverine, Idanpramine, Proxazole, Alverine, Trepibutone, Isometheptene, Caroverine, Phloroglucinol, Silicones, Trimethyldiphenylpropylamine Atropine, Hyoscyamine Scopolamine (Butylscopolamine, Methylscopolamine), Methylatropine, Fentonium, Cimetropium bromide primarily dopamine antagonists (Metoclopramide/Bromopride, Clebopride, Domperidone, Alizapride), 5-HT4 agonists (Cinitapride, Cisapride), Proton pump inhibitors Omeprazole, lansoprazole, pantoprazole, esomeprazole, rabeprazole sodium, opioids and opiod receptor antagonists—e.g. codeine, morphine, loperamide, diphenoxylate, methylnaltrexone bromide Analgesic Acetaminophen Diclofenac Diflunisal Etodolac Fenoprofen Flurbiprofen Ibuprofen Indomethacin Ketoprofen Ketorolac Meclofenamate Mefenamic Acid Meloxicam Nabumetone Naproxen Oxaprozin Phenylbutazone Piroxicam Sulindac Tolmetin Celecoxib Buprenorphine Butorphanol Codeine Hydrocodone Hydromorphone Levorphanol Meperidine Methadone Morphine Nalbuphine Oxycodone Oxymorphone Pentazocine, Propoxyphene Tramadol codeine Sleep Drugs Hypnotics—Nitrazepam, Flurazepam, Loprazolam, Lormetazepam, Temazepam, Zaleplon, Zolpidem, Zopiclone, Chloral Hydrate, Triclofos, Clomethiazole, Quazepam, triazolam Estazolam Clonazepam, Alprazolam, Eszopiclone, Rozerem, Trazodone, Amitriptyline Doxepin, Benzodiazepine drugs, melatonin, diphenhydramine and herbal remedies such as Valerian Cardiovascular Medicines Cardiac glycosides—Digoxin, digitoxin, Phosphodiesterase Inhibitors—enoximone, milrinone Thiazides and related diuretics—bendroflumethiazide, chlortalidone, cyclopenthiazide, inapamide, metolazone, xipamide Diuretics—furosemide, bumetanide, torasemide, Potassium sparing diuretics and aldosterone antagonists—amiloride hydrochloride, triamterene, weplerenone, spironolactone, Osmotic diuretics—mannitol Drugs for arrhythmias—adenosine, amiodarone hydrochloride, disopyramide, flecainide acetate, propafenone hydrochloride, lidocaine hydrochloride, Beta adrenoreceptor blocking drugs—propanalol, atenolol, acebutolol, bisprolol fumarate, carvedilol, celiprolol, esmolol, lebatolol, metoprolol tartrate, nadolol, nebivolol, oxprenolol, pindolol, solatol, timolol, Hypertension—ambrisentan, bosentan, diazoxide, hydralazine, iloprost, minoxidil, sildenafil, sitaxentan, sodium nitroprusside, clonidine, methyldopa, moxonidine, guanethidine monosuiphate, doxazosin, indoramin, prazosin, terazosin, phenoxybenzamine, phentolamine mesilate, Drugs affecting the renin-angiotensin system—Captropril, Cilazapril, Enalapril Maleate, Fosinopril, Imidapril, Lisinopril, Moexipril, Perindopril Erbumine, Quinapril, Ramipril, Trandolapril, Candesartan Cilexetil, Eprosartan, Irbesartan, Losartan, Olmesartan Medoxomil, Telmisartan, Valsartan, Aliskiren.

Nitrates, calcium channel Blockers and antianginal drugs—Glyceryl trinitrate, Isosorbide Dinitrate, Isosorbide Mononitrate, Amlodipine, Diltiazem, Felodipine, Isradipine, Lacidipine, Lercanidipine, Nicardipine, Nifedipine, Nimodipine, Verapamil, Ivabradine, Nicorandil, Ranolazine, Peripheral Vasodilators and related drugs—Cilostazol, Inositol Nicotinate, Moxisylyte, Naftidrofuryl Oxalate, Pentoxifylline, Sympathomimetics—Dopamine, Dopexamine, Ephedrine, Metaraminol, Noradrenaline Acid Tartrate, Norephidrine Bitartrate, Phenylephidrine, Anticoagulants and Protamine—Heparin, Bemiparin, Dalteparin, Enoxaparin, Tinzaparin, Danaparoid, Bivalirudin, Lepirudin, Epoprostenol, Fondaprinux, Warfarin, Acenocoumarol, Phenindione, Dabigatran Etexilate, Rivaroxaban, Protamine Sulphate, Antiplatelet Drugs—Abciximab, Asprin, Clopidogrel, Dipyridamole, Eptifibatide, Prasugrel, Tirofiban, Fibrinolytic and antifibrinolytic Drugs—Alteplase, Reteplase, Streptokinase, Tenecteplase, Urokinase, Etamsylate, Tranexamic Acid, Lipid Regulating Drugs—Atorvastatin, Fluvastatin, Pravastatin, Rosuvastatin, Simvastatin, Colesevam, Colestyramine, Colestipol, Ezetimibe, Bezafibrate, Ciprofibrate, Fenofibrate, Gemfibrozyl, Acipmox, Nictotinic Acid, Omega three fatty acid compounds, Ethanolamine Oleate, Sodium Tetradecyl Suphate.

CNS Drugs—Benperidol, Chlorpromazine, Flupentixol, Haloperidol, Levomepromazine, Pericyazine, Perphenazine, Pimozide, Prochlorperazine, Promazine, Sulpiride, Trifluoperazine, Zuclopenthixol, Amisulpride, Aripiprazole, Clozapine, Olanzapine, Paliperidone, Quetiapine, Riperidone, Sertindole, Zotepine, Flupentixol, Fluphenazine, Olanzapine Embonate, Pipotiazine Palmitate, Risperidone, Zuclopenthixol Decanoate, Carbamazepine, Valproate, Valproic acid, Lithium Carbonate, Lithium Citrate, Amitriptyline, Clomipramine, Dosulepin, Imipramine, Lofepramine, Nortriptyline, Trimipramine, mianserin, Trazodone, Phenelzine, Isocarboxazid, Tranylcypromine, Moclobemide, Citalopram, Escitalopram, Fluoxetine, Fluvoxamine, Paroxetine, Sertraline, Agomelatine, Duloxetine, Flupentixol, Mirtazapine, Reboxetine, Trytophan, Venflaxine, Atomoxetine, Dexametamine, Methylphenidate, Modafinil, Eslicarbazepine, Ocarbazepene, Ethosuximide, Gabapentin, Pregabalin, Lacosamide, Lamotrigine, Levetiracetam, Phenobarbital, Primidone, Phenytoin, Rufinamide, Tiagabine, Topiramate, Vigabatrin, Zonisamide, ropinirole, Rotigotine, Co-Beneldopa, Levodopa, Co-Careldopa, Rasagiline, Selegiline, Entacapone, Tolcapone, Amantidine, Orphenadrine, Procyclidine, Trihexyphenidyl, Haloperidol, Piracetam, Riluzole, Tetrabenazine, Acamprosate, Disulfiram, Bupropion, Vareniciline, Buprenorphine, Lofexidine, Donepezil, Galantamine, Memantine, Rivastigimine.

Anti-Infectives—Benzylpenicillin, Phenoxymethylpenicillin, Flucloxacillin, Temocillin, Amoxicillin, Ampicillin, Co-Amoxiclav, Co-Fluampicil, Piperacillin, Ticarcillin, Pivmecillinam, Cephalosporins, Cefaclor, Cefadroxil, Cefalexin, Cefixime, Cefotaxime, Cefradine, Ceftazidime, Cefuroxime, Ertapenem, Imipenem, Meropenem, Aztreonam, Tetracycline, Demeclocycline, Doxocycline, Lymecycline, Minocycline, Oxytetracycline, Tigecycline, Gentamicin, Amikacin, Neomycin, Tobramycin, Erythromycin, Azithromycin, Clarithromycin, Telithromycin, Clindamycin, Chloramphenicol, Fusidic Acid, Vancomycin, Teicoplanin, Daptomycin, Linezolid, Quinupristin, Colistin, Co-Trimoxazole, Sulpadiazine, Trimethoprim Capreomycin, Cycloserine, Ethambutol, Isoniazid, Pyrazinamide, Rifabutin, Rifampicin, Streptomycin, Dapsone, Clofazimine, Metronidazole, Tinidazole, Ciproflaxacin, Levoflaxacin, Moxifloxacin, Nalidixic Acid, Norflaxine, Orflaxacin, Nitrofurantoin, Methenamine Hippurate, Amphotericin, Anidulafungin, Caspofungin, Fluconazole, Flucytosine, Griseofluvin, Itraconzole, Ketoconazole, Micafungin, Nystatin, Posaconazole, Terbinafine, Voriconazole, Abacavir, Didanosine, Emtricitabine, Lamivudine, Stavudine, Tenofovir Disoproxil, Zidovudine, Atazanavir, Darunavir, Fosamprenavir, Indinavir, Lopinair, Nelfinavir, Ritonavir, Saquinavir, Tipranavir, Efavirenz, Etravirine, Nevarapine, Enfuvirtide, Maraviroc, Raltegravir, Aciclovir, Famciclovir, Inosine Pranobex, Valaciclovir, Cidofovir, Gangciclovir, Foscarnet, Valgangciclovir, Adefovir Dipivoxil, Entecavir, Telbivudine, Amantadine, Oseltamivir, Zanamivir, Palivizumab, Ribavirin, Artemether, Chloroquine, MefloquinePrimaquine, Proguanil, Pyrimethamine, Quinine, Doxycyclin, Diloxanide Furoate, Metronidaziole, Tinidazole, MepacrineSodium Stibogluconate, Atovaquone, Pentamidine Isetionate, Mebendazole, Piperazine, Other:

Benztropine, procyclidine, biperiden, Amantadine, Bromocriptine, Pergolide, Entacapone, Tolcapone, Selegeline, Pramipexole, budesonide, formoterol, quetiapine fumarate, olanzapine, pioglitazone, montelukast, Zoledromic Acid, valsartan, latanoprost, Irbesartan, Clopidogrel, Atomoxetine, Dexamfetamine, Methylphenidate, Modafinil, Bleomycin, Dactinomycin, Daunorubicin, Idarubicin, Mitomycin, Mitoxantrone, Azacitidine, Capecitabine, Cladribine, Clofarabine, Cytarabine, Fludarabine, Flourouracil, Gemcitabine, mercaptopurine, methotrexate, Nelarabine, Pemetrexed, Raltitrexed, Thioguanine, Apomorphine, Betamethasone, Cortisone, Deflazacort, Dexamethosone, Hydrocortisone, Methylprednisolone, Prednisolone, Triamcinolone, Ciclosporine, Sirolimus, Tacrolimus, Interferon Alpha, Interferon.

In a particularly preferred embodiment the active agent is designed to treat cardiovascular conditions, such as hypertension, angina pectoris and cardiac arrhythmia and as such the active agent is a cardiovascular agent, such as verapamil.

The term "active agent" is understood to include solvates (including hydrates) of the free compound or salt, crystalline and non-crystalline forms, as well as various polymorphs. For example, the active agent can include all optical isomers of the compounds and all pharmaceutically acceptable salts thereof either alone or in combination threo isomers can be indicated as "threo" and the combined erythro isomers as "erythro".

In accordance with the invention, formulations are provided which are to be taken by a subject and which do not initially administer the active agent when the subject first takes the formulation. However, at a later time point the agent is administered to the subject in a prolonged manner over a period of time.

In relation to the treatment of cardiovascular conditions, it is known that many complications often occur early in the morning, soon after a patient wakes up. Thus, it is desirable to be able to provide a cardiovascular agent before a patient wakes up and during the hours following awakening. It is with this in mind, that the present inventors sought to develop formulations which are designed to release a cardiovascular agent prior to a patient waking up and for a period thereafter. Such formulations would be designed to be taken prior to the subject going to bed the night before and would have to display a significant delay in release of the cardiovascular agent. This has been achieved with the press-coated tablet formulations of the present invention.

LH-32 is a particular type of low substituted hydroxypropyl cellulose (L-HPC) and may be obtained from Shin-Etsu Chemical Co., Ltd., Tokyo, Japan. L-HPCs are insoluble in water and comprise a glucose backbone which is substituted to a minimal extent by hydroxypropyl groups. LH-32 is micronised, with a mean particle diameter of 20 μm LH-32 has a molecular weight of 115,000 and a hydroxypropyl cellulose content of 8%.

The wax for use in the core and the delayed release layer may be any suitable wax such as beeswax, carnuba wax, microcrystalline wax, hydrogenated castor oil. A particularly preferred wax is a glyceryl ester, such as glycerol behenate. The wax in the core and the delayed release layer may be the same or different.

In a preferred formulation of the present invention as defined herein above, the wax and LH-32 are present in a ratio of 25:75 to 40:60 w/w. More preferably the ratio is 25:75 to 35:65 w/w, or 30:70 w/w. The skilled addressee will appreciate that with appropriate variation of the ratio, the delay in drug release can be tailored for a particular application. For example, a 30:70 w/w ratio of glycerol behenate as a wax, with LH-21 as the L-HPC employed as a delayed release layer in accordance with the present invention, is observed to provided a delayed release of approximately 1 hour. However, the same ratio with LH-32 as the L-HPC provides a delay in release of only 3 hours. Thus with appropriate control of the ratio of wax to LH-32, it is possible to control the time delay in release of the active agent, from a press-coated tablet comprising a delayed release layer surrounding a core comprising the active agent.

The delayed release layer surrounding the core may also comprise an amount of an active agent or agents, which may be the same or different to the active agent in the core and/or top layer, and which is designed to be released during dissolution/disintegration of the delayed release layer.

The subject to be treated is an animal, e.g. a mammal, especially a human.

The amount of active agent to be administered will be sufficient to be therapeutic or prophylactic. By therapeutic or prophylactic is meant one capable of achieving the desired response, and will be adjudged, typically, by a medical practitioner. The amount required will depend upon one or more of at least the active compound(s) concerned, the patient, the condition it is desired to treat or prevent and the formulation. However, it is likely to be in the order of from 1 µg to 1 g of compound per kg of body weight of the patient being treated.

Different dosing regimes may likewise be administered, again typically at the discretion of the medical practitioner. The formulation of the present invention may allow for at least daily administration although regimes where the compound(s) is (or are) administered more infrequently, e.g. every other day, weekly or fortnightly, for example, are also embraced by the present invention.

By treatment is meant herein at least an amelioration of a condition suffered by a patient; the treatment need not be curative (i.e. resulting in obviation of the condition). Analogously references herein to prevention or prophylaxis herein do not indicate or require complete prevention of a condition; its manifestation may instead be reduced or delayed via prophylaxis or prevention according to the present invention.

For use according to the present invention, the compounds or physiologically acceptable salt, solvate, ester or other physiologically acceptable functional derivative thereof described herein are presented in a press-coated tablet form comprising the compound or physiologically acceptable salt, ester or other physiologically functional derivative thereof, together with one or more pharmaceutically acceptable excipients therefore and optionally other therapeutic and/or prophylactic ingredients. Any excipients are acceptable in the sense of being compatible with the other ingredients of the formulation and not deleterious to the recipient thereof.

The tablets of the present invention may be prepared using reagents and techniques readily available in the art and/or exemplary methods as described herein.

The tablets include those suitable for oral, rectal or vaginal administration. The tablets may, where appropriate, be conveniently presented in discrete dosage units and may be prepared by any of the methods well known in the art of pharmacy.

Compressed tablets may be prepared by compressing in a suitable machine an active compound in a free-flowing form such as a powder or granules together with the wax, optionally mixed with a binder, lubricant, inert diluent, lubricating agent, surface-active agent or dispersing agent, together with the materials for forming the delayed release layer. Tablets may be optionally coated (for example by a gastro-resistant coating) or uncoated.

Tablets suitable for rectal administration are most preferably presented as unit dose suppositories. Suitable carriers include cocoa butter and other materials commonly used in the art. The suppositories may be conveniently formed by admixture of a tablet with the softened or melted carrier(s) followed by chilling and shaping in moulds.

The tablets of the present invention may be prepared using pharmaceutical processes namely by direct compression or by granulation processing and final tableting. The process may comprise the steps of initially forming a core comprising the active agent and subsequently surrounding core with the delayed release layer. The core may be formed by dispersing one or more active agents with the melted wax, optionally with one or more excipients, such as lactose. The resulting material may be granulated or forced through a sieve in order to obtain granules of a desired size, such as 500 µm to 1 mm.

The delayed release layer may be formed by melting the wax component and subsequently admixing the other components including the LH-32. The mixture may then be allowed to cool and solidify before being ground and/or forced through a sieve, in order to achieve granules of the size range 500 µm-1 mm. The core may then be coated with the delayed release layer material by direct compression. Typically the core is sandwiched between top and bottom layers of the delayed release material and hence completely surrounds the core.

At the same time, the top-coating layer, if present, may be press-coated on top of the delayed release layer. The top-coating may be formed by blending together the active agent(s) and one or more excipients, such as a sugar (e.g. lactose) and a L-HPC, such as LH-21.

The tableting for the formulation of tablets may be conducted using an apparatus ordinarily employed for the formation or granulation of tablets. Examples may include single-punch tableting machine, rotary tableting machine and tableting tester.

Tableting is conducted usually under a pressure of 50 to 300 MPa, preferably 80 to 200 MPa. At a pressure less than 50 MPa, the resulting tablet may have insufficient hardness, which disturbs easily handling, while pressures exceeding 300 MPa may serve to cause a delay in disintegration.

The core and/or delayed release layer may include a filler, such as a water insoluble filler, water soluble filler, and mixtures thereof. The water insoluble filler, may be a calcium salt or talc. Exemplary water soluble fillers such as water soluble sugars and sugar alcohols, preferably lactose, glucose, fructose, mannose, galactose, the corresponding sugar alcohols and other sugar alcohols, such as mannitol, sorbitol, and xylitol.

The filler in the delayed release layer can be the same or different as the filler in the core composition, if any. For example, the core composition can include a water soluble filler while the press coat composition can include a water insoluble filler. For example, a water soluble/hydrophilic material, such as lactose may be included in the core to provide a hydrophilic balance with the hydrophobic wax component of the core. By adjustment of the water-soluble/hydrophilic material and wax, any desired slow release rate can be achieved.

Other excipients can also be present in the core and/or delayed release layer, including lubricants (such as talc and magnesium stearate), glidants (such as fumed or colloidal silica), pH modifiers (such as acids, bases and buffer systems), and pharmaceutically useful processing aids. It will be appreciated that such other excipients may be the same or different in the core and delayed release layer, if any.

In a preferred embodiment of the invention, the core components (active agent, wax and optional excipients) are blended together and compressed into suitable cores. The blending can take place in any preferred order of addition.

Preferably, the cores are blended by starting with the smallest volume component and then successively adding the larger volume components.

The tablet can be further coated with optional additional coatings. The additional coatings can be pH-dependent on pH-independent, aesthetic or functional; where the coating is a gastro-resistant coating (intented to prevent release in the stomach), the 'clock' or time for delayed release, as defined herein, will not start until gastric emptying occurs and dissolution of the gastro-resistant coating takes place (as can be determined, for example, by employing scintigraphy studies). The time taken for dissolution of the gastro-resistant coating together with the delay from the time-delay layer will ensure drug release in the lower reaches of the intestine, particularly the distal ileum and/or colon. Such additional coatings preferably include film forming materials.

DETAILED DESCRIPTION

The present invention will now be further described by way of example and with reference to the figures which show:

CLINICAL NEED

This formulation is designed to be taken at night, with slow release of the verapamil after a 3-4 hour delay. Complete release is achieved after approximately 7 hours which ensures the drug is available continuously during both the pre-wake up and wake up period when there is the greatest cardiovascular clinical need.

Methods

Core Tablet Blend and Core Tablet Compression
(194.5 mg Verapamil HCl=180 mg Verapamil)
(i) Verapamil and excipients weighed into tared weigh boats according to Table 1.

TABLE 1

| API/Excipient | Weight (g) |
|---|---|
| Verapamil HCl | 5.835 |
| Glycerol behenate (GB) | 0.7 |
| Lactose | 0.7 |

(ii) GB placed in a glass beaker on a hot plate set at 100° C. Once the GB melted, the lactose and Verapamil HCl are added gradually whilst stirring until a sticky granular mass is achieved.
(iii) The mix taken off the hotplate and stirred continuously until cooled to room temperature. The granules are left for at least 30 min at room temperature before the next step.
(iv) The cooled granules forced through a 1 mm sieve (using a spatula and a brush) and collected on a 500 μm sieve so that the granules used are in the size range 500 μm-1 mm.
(v) Granules stored in amber glass screw-top jar until use.
(vi) For 6 core tablets, 6×234.5 mg core tablet granules weighed into tared weigh boats and compressed in 10 mm die/punch set for 1 minute at 2 tons.

Granules (to Surround Core Tablet)
(i) Glycerol behenate and LH-32 weighed into tared weigh boats according to Table 2:

TABLE 2

| Excipient | Weight (g) |
|---|---|
| GB | 6 |
| LH-32 | 14 |

(ii) GB placed in a glass beaker on a hot plate set at 100° C. Once the GB melted, LH-32 added gradually whilst stirring until a uniform mix is achieved.
(iii) The mix stirred continuously until cooled to room temperature. The granules are left for at least 30 min at room temperature before the next step.
(iv) The cooled granules forced through a 1 mm sieve (using a spatula and a brush) and collected on a 500 μm sieve so that the granules used are in the size range 500 μm-1 mm.
(v) Granules stored in amber glass screw-top jar until use.

Formulation Compression
(i) A 13 mm die and matching flat-faced punches used to compress the formulation. For 6 tablets, 12×250 mg granules (to surround core tablet) are weighed into tared weigh boats.
(ii) 250 mg granules placed onto the lower punch, core tablet dropped on and centralised before placing the other 250 mg granules on top.
(iii) The formulation compressed at 5 ton for 2 minutes in a 13 mm die/punch set.

Dissolution
Dissolution performed in 900 ml sodium phosphate buffer (0.01 M, pH 7) at 37° C., with UV analysis at 279 nm.

Figure 1:
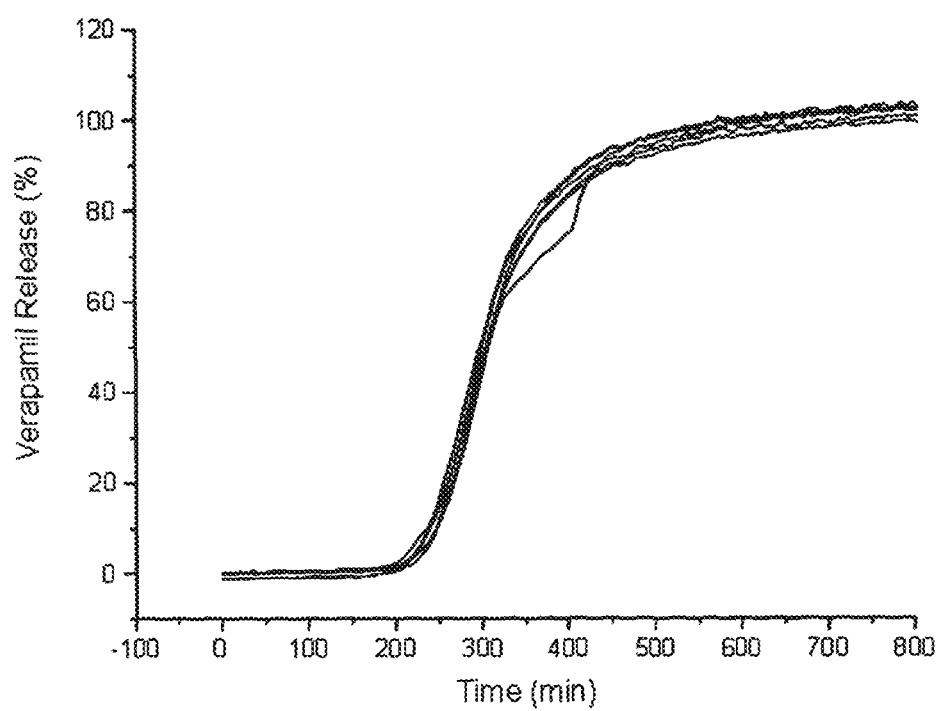
FIG. 1 shows the release profile of a drug from a tablet comprising glycerol behenate and LH-32 in a 30:70 w/w ratio in a delayed release layer.

Results (30:70, GB:LH-32)
As can be seen in FIG. 1, there is a delay in release of verapamil of about 3.5 hours, with substantially (i.e. >90%) all the verapamil being released by about 7 hours.

Figure 2:
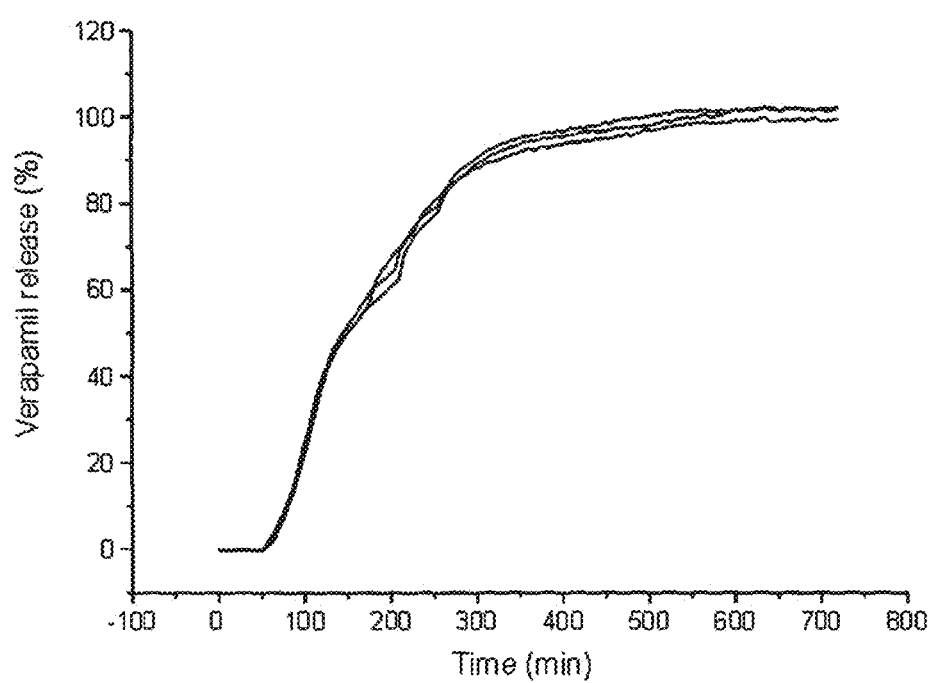
FIG. 2 shows the release profile of a drug from a tablet comprising glycerol behenate and LH-21 in a 30:70 w/w ratio in a delayed release layer.

Supporting Data
LH-21 instead of LH-32 (30:70, GB:LH-21)
As can be seen in FIG. 2, substituting LH-21 for LH-32, shortens the period of delay, to approximately 1 hour, with substantially (i.e. >90%) all the verapamil being released within 6 hours.

This profile shows a dramatically shortened delay time before drug release commences which renders this inappropriate for our chosen application where the four hour delay before drug release is essential.

Extraction Method/Analysis of Plasma levels of Verapamil
Materials
Human plasma, lithium heparin, origin USA: Sera laboratories international Ltd, Bx H911239 Verapamil HCl
Norverapamil HCl, Sigma Aldrich, lot 019K46152
DEE: Fisher laboratory reagent grade Bx 1097413
Methods
Calibration:
vortex blank plasma
add 400 ul blank plasma to glass screw cap tubes using gilson pipette
blank preparation—to be prepped before standards
add 100 ul mobile phase to 400 ul blank plasma
vortex 10 secs add 4 mL DEE and vortex 3 mins (note: DEE decanted from bottle fresh every day
pipette tips changed after every addition of mobile phase/DEE Standard Preparation:
starting with lowest concentration standard, vortex standard 10 secs to mix
add 100 ul standard to 400 uL blank plasma
vortex 10 secs
add 4 mL DEE and vortex 3 mins (note: DEE decanted from bottle fresh every day)
pipette tips changed after every addition of standard/DEE
centrifuge samples 3 mins at 2000 rpm
remove top layer into clean labelled glass screwtop tube using glass pipette
evaporate to dryness under nitrogen at 40° C.
reconstitute in 100 ul mobile phase. Allow to stand for 30 mins and then vortex 3 mins
transfer to HPLC vial with insert Mobile Phase Preparation:
Materials
potassium phosphate monobasic, SAFC lot 1370660
acetonitrile: Fisher HPLC gradeBx 1095614
orthophosphoric acid: Analar normapur Bx 08J170519
25 mM potassium phosphate buffer prepared with Q3 water, adjusted to pH 2.5 with orthophosphoric acid
Buchner filtered through 0.2 um 47 mm nylon membrane Chromatographic Conditions
Gynkotek HPLC system with perkin elmer LS 40 fluorescence detector
Column: phenomenex Gemini C6-Phenyl 110A 250×4.6 mm 5 micron with guard column
Detection: excitation: 280 nm emission:313 nm
Isocratic 30.5% acetonitrile 69.5% phosphate buffer, flow rate 1 mL/min, run time 20 mins
Injection volume 20 uL Standard Range:
verapamil 10-500 ng/mL plasma
norverapamil 8.6-428 ng/mL plasma Clinical Trial Protocol—Verapamil 180 mg sustained-release over 6-8 hours (3 hour time-delay)

Clinical studies were carried out in Healthy male volunteers aged between 18-65 years inclusive with a body mass index (BMI) between 18.0 and 29.9 kg/m². Each subject received the following delayed-release tablets: Each tablet was radiolabelled with 4 MBq 99mTc-DTPA and administered with 240 ml of water at bedtime.

Subjects received a standard dinner comprising roast chicken with salad, low fat yoghurt and one cup of decaffeinated tea, coffee or juice 2 hours prior to dosing.

Gastrointestinal transit of the delayed-release tablets was characterised by inclusion of a radiolabel marker, technetium-99m ($^{99m}$Tc), complexed with diethylenetriaminepentaacetic acid (DTPA) which prevents absorption from the gastrointestinal tract. The radiolabel is incorporated into the core tablet. Each tablet was radiolabelled with 4 MBq 99mTc-DTPA and administered with 240 ml of water at bedtime.

Scintigraphic imaging was performed using a Siemens E-Cam gamma camera fitted with a low-energy high-resolution collimator. Subjects were imaged in a standing position except during periods of sleep where the subjects were imaged lying down. Anterior static acquisitions of 25-second duration each were collected immediately after dosing then every 30 minutes until 1 hour post-dose then every 15 minutes until complete release of radiolabel marker.

Figure 3:
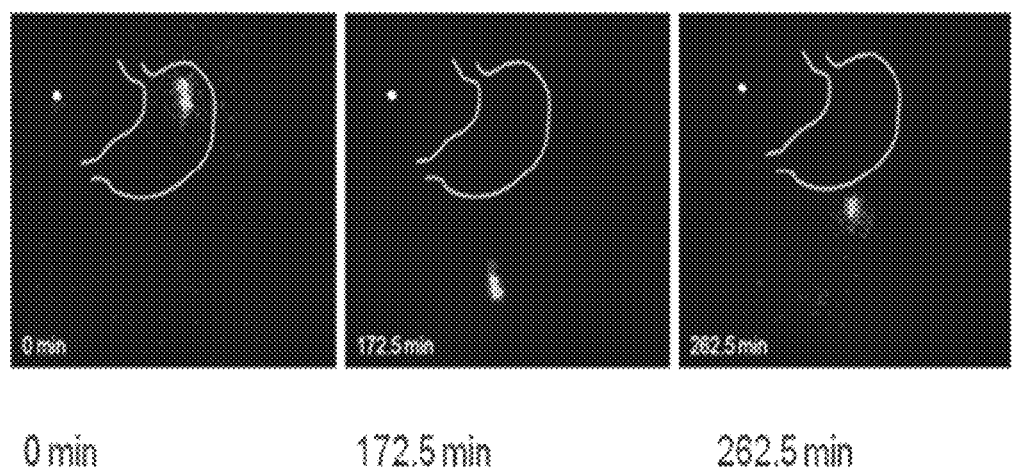
FIG. 3 shows Gamma Scintigraphy imaging of In-vivo release of controlled release Verapamil formulation.

A 5 mL pre-dose blood sample was taken from each subject 15 minutes before dosing. Following dosing blood samples were taken every 30 minutes until burst release observed by scintigraphy then every 15 minutes for 2 hours then every 30 minutes for 1 hour then hourly until end of study day (15 hours post-dose). See FIG. 3.

Figure 4:
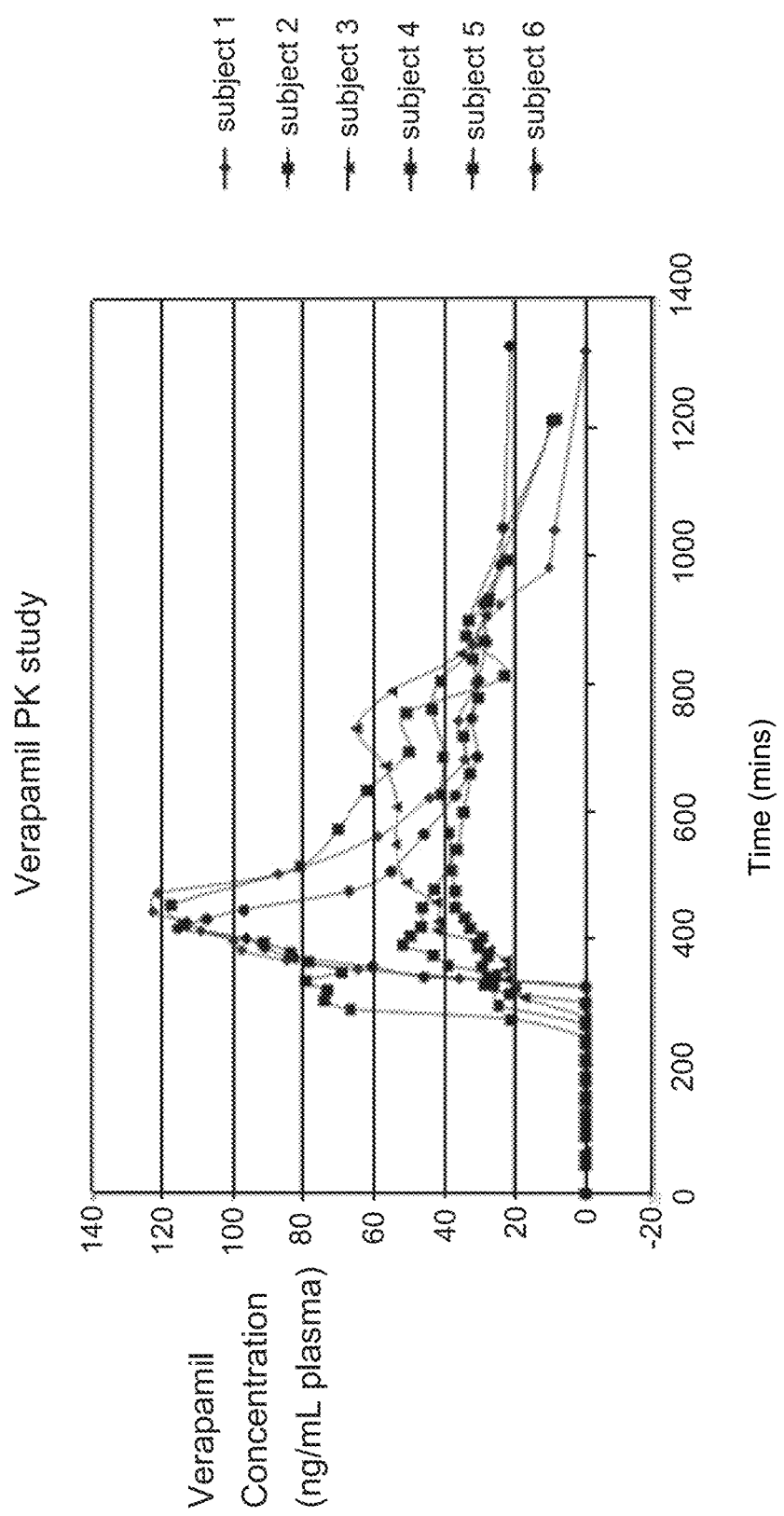
FIGS. 4 and 5 show Pharmacokinetic analysis of Verapamil and norverapamil levels in plasma, in 6 subjects. Verapamil is quickly metabolized to its active metabolite nor-Verapamil so both variants were measured in blood plasma.
Figure 5:
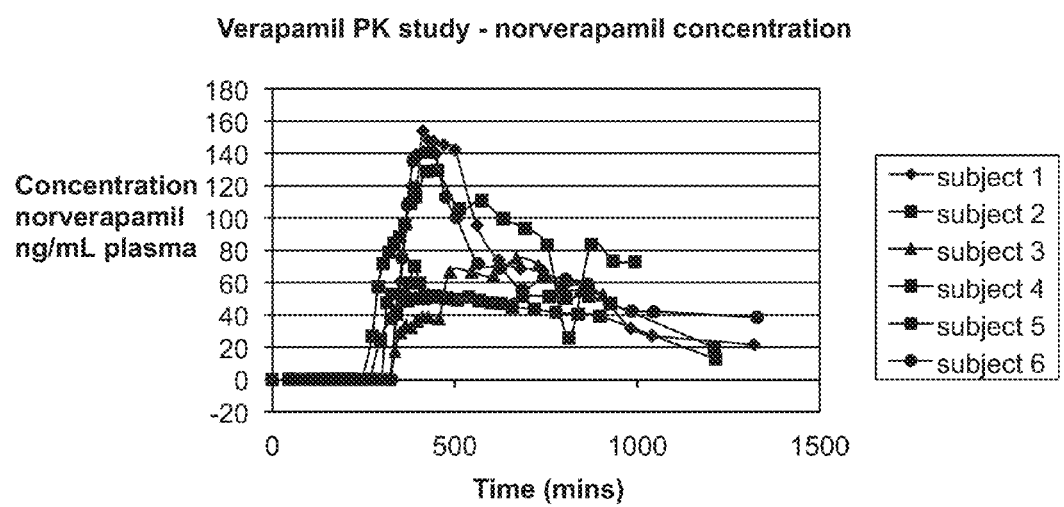

Blood samples were centrifuged at 2000 g for 10 minutes and the plasma fraction removed and stored at −20° C. for subsequent analysis. See FIGS. 4 and 5.

The invention claimed is:

1. A press-coated tablet formulation for a delayed, followed by a prolonged release of an active agent, the press-coated tablet formulation comprising:
   (a) a core comprising the active agent together with a wax and optionally one or more fillers; and
   (b) a delayed release layer surrounding the core and comprising a wax and a low substituted hydroxypropyl cellulose in a ratio of 20:80 to 50:50 w/w; wherein the delayed release layer delays release of the active agent within the core for between 2-8 hours after administration of the press-coated tablet formulation to a subject and thereafter a prolonged release of the active agent from the core occurs, such that the active agent in the core is continuously released over a period of 2 up to 8 hours and wherein the low substituted hydroxypropyl cellulose is micronised with a mean particle diameter of 20 μm and has a molecular weight of 115,000 and a hydroxypropyl content of 8%.

2. The press-coated tablet formulation according to claim 1, further comprising:
   (c) a top-coating layer comprising an active agent together with one or more excipients, wherein at least 70% of the active agent in the top-coating layer is released within 5-45 minutes following administration to the subject of the press-coated tablet formulation.

3. The press-coated tablet formulation according to claim 2 further comprising an amount of an active agent, which is the same or different to the active agent in the core and/or top-coating layer, in the delayed release layer.

4. The press-coated tablet formulation according to claim 2 wherein at least 80% of the active agent in the top-coating layer is released within 5-45 minutes following administration to the subject of the press-coated tablet.

5. The press-coated tablet formulation according to claim 4, wherein at least 80% of the active agent in the top-coating layer is released within 10-30 minutes following administration to the subject of the press-coated tablet formulation.

6. The press-coated tablet formulation according to claim 2, wherein at least 90% of the active agent in the top-coating layer is released within 5-45 minutes following administration to the subject of the press-coated tablet formation.

7. The press-coated tablet formulation according to claim 6, wherein at least 90% of the active agent in the top-coating layer is released within 10-30 minutes following administration to the subject of the press-coated tablet formulation.

8. The press-coated tablet formulation according to claim 2, wherein at least 70% of the active agent in the top-coating layer is released within 10-30 minutes following administration to the subject of the press-coated tablet formulation.

9. The press-coated tablet formulation according to claim 1 wherein the active agent is designed to treat cardiovascular conditions selected from the group consisting of hypertension, angina pectoris and cardiac arrhythmia.

10. The press-coated tablet formulation according to claim 9 wherein the press-coated tablet formulation comprises verapamil.

11. The press-coated tablet formulation according to claim 1 wherein the wax for use in the core and the delayed release layer is independently selected from beeswax, carnuba wax, microcrystalline wax, hydrogenated castor oil and a glyceryl ester.

12. The press-coated tablet formulation according to claim 11 wherein the glyceryl ester is glycerol behenate.

13. The press-coated tablet formulation according to claim 11 wherein the wax in the core and the delayed release layer is the same or different.

14. The press-coated tablet formulation according to claim 1 wherein the wax in the delayed release layer and the low substituted hydroxypropyl cellulose are present in a ratio of 25:75 to 40:60 w/w.

15. The press-coated tablet formulation according to claim 1 further comprising one or more pH-dependent, pH-independent, aesthetic or functional coatings.

16. The press-coated tablet formulation according to claim 15 wherein the coating is a gastro-resistant coating.

17. The press-coated tablet formulation according to claim 1 wherein the active agent in the core is continuously released over a period of 3-6 hours.

18. The press-coated tablet formulation according to claim 1 wherein less than 10% of the active agent within the core is released for between 2-8 hours after administration of the press-coated tablet formulation tablet to the subject.

19. The press-coated tablet formulation according to claim 18 wherein less than 5% of the active agent within the core is released for between 2-8 hours after administration of the press-coated tablet formulation tablet to the subject.

20. The press-coated tablet formulation according to claim 18 wherein less than 1% of the active agent within the core is released for between 2-8 hours after administration of the press-coated tablet formulation tablet to the subject.

21. The press-coated tablet formulation according to claim 1, comprising one or more of the following active agents:
  Antacids selected from the group consisting of aluminium hydroxide, magnesium carbonate, magnesium trisilicate, hydrotalcite, and simeticonealginates;
  Antispasmodics selected from the group consisting of atropine sulphate, dicycloverine hydrochloride, hyoscine butylbromine, propantheline bromide, alverine citrate, and mebeverine hydrochloride;
  Motility stimulants selected from the group consisting of metoclorpramide and domperidone;
  H2-Receptor antagonists selected from the group consisting of Cimetidine, famotidinenizatidine, and ranitidine;
  Antimuscarinics;
  Chelates selected from the group consisting of Tripotassium dicitratbismuthate and sucralfate;
  Prostaglandin analogues;
  Aminosalicylates selected from the group consisting of balsazide sodium, mesalazine, olsalazine, and sulphasalazine;
  Corticosteroids selected from the group consisting of beclometasone dipropionate, budenoside, hydrocortisone, and prednisolone;
  Affecting immune response selected from the group consisting of ciclosporin, mercaptopurine, methotrexate, adalimumab, and infliximab;
  Stimulant laxatives selected from the group consisting of bisacodyl, dantron, docusate, and sodium picosulfate;
  Drugs affecting biliary composition and flow;
  Bile acids sequestrants selected from the group consisting of colestyramine, Oxyphencyclimine, Camylofin, Mebeverine, Trimebutine, Rociverine, Dicycloverine, Dihexyverine, Difemerine, Piperidolate, Benzilone, Mepenzolate, Pipenzolate, Glycopyrronium, Oxyphenonium, Penthienate, Methantheline, Propantheline, Otilonium bromide, Tridihexethyl, Isopropamide, Hexocyclium, Poldine, Bevonium, Diphemanil, Tiemonium iodide, Prifinium bromide, Timepidium bromide, Fenpiverinium, Papaverine, Drotaverine, Moxaverine, 5-HT3 antagonists, 5-HT4 agonists, Fenpiprane, Diisopromine, Chlorbenzoxamine, Pinaverium, Fenoverine, Idanpramine, Proxazole, Alverine, Trepibutone, Isometheptene, Caroverine, Phloroglucinol, Silicones, Trimethyldiphenylpropylamine, Atropine, Hyoscyamine, Scopolamine, Butylscopolamine, Methylscopolamine, Methylatropine, Fentonium, Cimetropium bromide, and primarily dopamine antagonists;
  Proton pump inhibitors selected from the group consisting of Omeprazole, lansoprazole, pantoprazole, esomeprazole, and rabeprazole sodium;
  Opioids and opioid receptor antagonists;
  Analgesics selected from the group consisting of Acetaminophen, Diclofenac, Diflunisal, Etodolac, Fenoprofen, Flurbiprofen, Ibuprofen, Indomethacin, Ketoprofen, Ketorolac, Meclofenamate, Mefenamic Acid, Meloxicam, Nabumetone, Naproxen, Oxaprozin, Phenylbutazone, Piroxicam, Sulindac, Tolmetin, Celecoxib, Buprenorphine, Butorphanol, Codeine, Hydrocodone, Hydromorphone, Levorphanol, Meperidine, Methadone, Morphine, Nalbuphine, Oxycodone, Oxymorphone, Pentazocine, Propoxyphene, and Tramadol;
  Sleep drugs selected from the group consisting of Nitrazepam, Flurazepam, Loprazolam, Lormetazepam, Temazepam, Zaleplon, Zolpidem, Zopiclone, Chloral Hydrate, Triclofos, Clomethiazole, Quazepam, triazolam, Estazolam, Clonazepam, Alprazolam, Eszopiclone, Rozerem, Trazodone, Amitriptyline, Doxepin, Benzodiazepine drugs, melatonin, diphenhydramine, and herbal remedies;
  Cardiac glycosides selected from the group consisting of Digoxin and digitoxin;
  Phosphodiesterase Inhibitors selected from the group consisting of enoximone and milrinone;
  Thiazides and related diuretics selected from the group consisting of bendroflumethiazide, chlortalidone, cyclopenthiazide, inapamide, metolazone, and xipamide;
  Diuretics selected from the group consisting of furosemide, bumetanide, and torasemide;
  Potassium sparing diuretics and aldosterone antagonists selected from the group consisting of amiloride hydrochloride, triamterene, weplerenone, and spironolactone;
  Osmotic diuretics;
  Drugs for arrhythmias selected from the group consisting of adenosine, amiodarone hydrochloride, disopyramide, flecainide acetate, propafenone hydrochloride, and lidocaine hydrochloride;
  Beta adrenoreceptor blocking drugs selected from the group consisting of propranolol, atenolol, acebutolol, bisoprolol fumarate, carvedilol, celiprolol, esmolol, lebatolol, metoprolol tartrate, nadolol, nebivolol, oxprenolol, pindolol, solatol, and timolol;
  Hypertension drugs selected from the group consisting of ambrisentan, bosentan, diazoxide, hydralazine, iloprost, minoxidil, sildenafil, sitaxentan, sodium nitroprus side, clonidine, methyldopa, moxonidine, guanethidine monosulphate, doxazosin, indoramin, prazosin, terazosin, phenoxybenzamine, and phentolamine mesilate;
  Drugs affecting the renin-angiotensin system selected from the group consisting of Captropril, Cilazapril, Enalapril Maleate, Fosinopril, Imidapril, Lisinopril, Moexipril, Perindopril Erbumine, Quinapril, Ramipril, Trandolapril, Candesartan Cilexetil, Eprosartan, Irbesartan, Losartan, Olmesartan Medoxomil, Telmisartan, Valsartan, and Aliskiren;

Nitrates, calcium channel Blockers, and antianginal drugs selected from the group consisting of Glyceryl trinitrate, Isosorbide Dinitrate, Isosorbide Mononitrate, Amlodipine, Diltiazem, Felodipine, Isradipine, Lacidipine, Lercanidipine, Nicardipine, Nifedipine, Nimodipine, Verapamil, Ivabradine, Nicorandil, and Ranolazine;

Peripheral Vasodilators and related drugs selected from the group consisting of Cilostazol, Inositol Nicotinate, Moxisylyte, Naftidrofuryl Oxalate, and Pentoxifylline;

Sympathomimetics selected from the group consisting of Dopamine, Dopexamine, Ephedrine, Metaraminol, Noradrenaline Acid Tartrate, Norephidrine Bitartrate, and Phenylephidrine;

Anticoagulants and Protamine selected from the group consisting of Heparin, Bemiparin, Dalteparin, Enoxaparin, Tinzaparin, Danaparoid, Bivalirudin, Lepirudin, Epoprostenol, Fondaprinux, Warfarin, Acenocoumarol, Phenindione, Dabigatran Etexilate, Rivaroxaban, and Protamine Sulphate;

Antiplatelet Drugs selected from the group consisting of Abciximab, Asprin, Clopidogrel, Dipyridamole, Eptifibatide, Prasugrel, and Tirofiban;

Fibrinolytic and antifibrinolytic drugs selected from the group consisting of Alteplase, Reteplase, Streptokinase, Tenecteplase, Urokinase, Etamsylate, and Tranexamic Acid;

Lipid regulating drugs selected from the group consisting of Atorvastatin, Fluvastatin, Pravastatin, Rosuvastatin, Simvastatin, Colesevam, Colestyramine, Colestipol, Ezetimibe, Bezafibrate, Ciprofibrate, Fenofibrate, Gemfibrozyl, Acipmox, Nictotinic Acid, Omega three fatty acid compounds, Ethanolamine Oleate, and Sodium Tetradecyl Suphate;

CNS Drugs selected from the group consisting of Benperidol, Chlorpromazine, Flupentixol, Haloperidol, Levomepromazine, Pericyazine, Perphenazine, Pimozide, Prochlorperazine, Promazine, Sulpiride, Trifluoperazine, Zuclopenthixol, Amisulpride, Aripiprazole, Clozapine, Olanzapine, Paliperidone, Quetiapine, Riperidone, Sertindole, Zotepine, Flupentixol, Fluphenazine, Olanzapine Embonate, Pipotiazine Palmitate, Risperidone, Zuclopenthixol Decanoate, Carbamazepine, Valproate, Valproic acid, Lithium Carbonate, Lithium Citrate, Amitriptyline, Clomipramine, Dosulepin, Imipramine, Lofepramine, Nortriptyline, Trimipramine, mianserin, Trazodone, Phenelzine, Isocarboxazid, Tranylcypromine, Moclobemide, Citalopram, Escitalopram, Fluoxetine, Fluvoxamine, Paroxetine, Sertraline, Agomelatine, Duloxetine, Flupentixol, Mirtazapine, Reboxetine, Trytophan, Venflaxine, Atomoxetine, Dexametamine, Methylphenidate, Modafinil, Eslicarbazepine, Ocarbazepene, Ethosuximide, Gabapentin, Pregabalin, Lacosamide, Lamotrigine, Levetiracetam, Phenobarbital, Primidone, Phenytoin, Rufinamide, Tiagabine, Topiramate, Vigabatrin, Zonisamide, ropinirole, Rotigotine, Co-Beneldopa, Levodopa, Co-Careldopa, Rasagiline, Selegiline, Entacapone, Tolcapone, Amantidine, Orphenadrine, Procyclidine, Trihexyphenidyl, Haloperidol, Piracetam, Riluzole, Tetrabenazine, Acamprosate, Disulfiram, Bupropion, Vareniciline, Buprenorphine, Lofexidine, Donepezil, Galantamine, Memantine, and Rivastigimine;

Anti-Infectives selected from the group consisting of Benzylpenicillin, Phenoxymethylpenicillin, Flucloxacillin, Temocillin, Amoxicillin, Ampicillin, Co-Amoxiclav, Co-Fluampicil, Piperacillin, Ticarcillin, Pivmecillinam, Cephalosporins, Cefaclor, Cefadroxil, Cefalexin, Cefixime, Cefotaxime, Cefradine, Ceftazidime, Cefuroxime, Ertapenem, Imipenem, Meropenem, Aztreonam, Tetracycline, Demeclocycline, Doxocycline, Lymecycline, Minocycline, Oxytetracycline, Tigecycline, Gentamicin, Amikacin, Neomycin, Tobramycin, Erythromycin, Azithromycin, Clarithromycin, Telithromycin, Clindamycin, Chloramphenicol, Fusidic Acid, Vancomycin, Teicoplanin, Daptomycin, Linezolid, Quinupristin, Colistin, Co-Trimoxazole, Sulpadiazine, Trimethoprim, Capreomycin, Cycloserine, Ethambutol, Isoniazid, Pyrazinamide, Rifabutin, Rifampicin, Streptomycin, Dapsone, Clofazimine, Metronidazole, Tinidazole, Ciproflaxacin, Levoflaxacin, Moxifloxacin, Nalidixic Acid, Norflaxine, Orflaxacin, Nitrofurantoin, Methenamine Hippurate, Amphotericin, Anidulafungin, Caspofungin, Fluconazole, Flucytosine, Griseofluvin, Itraconzole, Ketoconazole, Micafungin, Nystatin, Posaconazole, Terbinafine, Voriconazole, Abacavir, Didanosine, Emtricitabine, Lamivudine, Stavudine, Tenofovir Disoproxil, Zidovudine, Atazanavir, Darunavir, Fosamprenavir, Indinavir, Lopinair, Nelfinavir, Ritonavir, Saquinavir, Tipranavir, Efavirenz, Etravirine, Nevarapine, Enfuvirtide, Maraviroc, Raltegravir, Aciclovir, Famciclovir, Inosine Pranobex, Valaciclovir, Cidofovir, Gangciclovir, Foscarnet, Valgangciclovir, Adefovir Dipivoxil, Entecavir, Telbivudine, Amantadine, Oseltamivir, Zanamivir, Palivizumab, Ribavirin, Artemether, Chloroquine, Mefloquine, Primaquine, Proguanil, Pyrimethamine, Quinine, Doxycyclin, Diloxanide Furoate, Metronidaziole, Tinidazole, Mepacrine, Sodium Stibogluconate, Atovaquone, Pentamidine Isetionate, Mebendazole, and Piperazine; and other drugs selected from the group consisting of Benztropine, procyclidine, biperiden, Amantadine, Bromocriptine, Pergolide, Entacapone, Tolcapone, Selegeline, Pramipexole, budesonide, formoterol, quetiapine fumarate, olanzapine, pioglitazone, montelukast, Zoledromic Acid, valsartan, latanoprost, Irbesartan, Clopidogrel, Atomoxetine, Dexamfetamine, Methylphenidate, Modafinil, Bleomycin, Dactinomycin, Daunorubicin, Idarubicin, Mitomycin, Mitoxantrone, Azacitidine, Capecitabine, Cladribine, Clofarabine, Cytarabine, Fludarabine, Flourouracil, Gemcitabine, mercaptopurine, methotrexate, Nelarabine, Pemetrexed, Raltitrexed, Thioguanine, Apomorphine, Betamethasone, Cortisone, Deflazacort, Dexamethosone, Hydrocortisone, Methylprednisolone, Prednisolone, Triamcinolone, Ciclosporine, Sirolimus, Tacrolimus, Interferon Alpha, and Interferon Beta.

22. The press-coated tablet formulation according to claim 21, comprising one or more of the following active agents:
pirenzepine, misoprostol, ursodeoxycholic acid, Alosetron, Cilansetron, Mosapride, Prucalopride, Tegaserod, Metoclopramide, Bromopride, Clebopride, Domperidone, Alizapride, Cinitapride, Cisapride, codeine, morphine, loperamide, diphenoxylate, methylnaltrexone bromide, Valerian, and mannitol.

23. A method of treating a cardiovascular condition, the method comprising administering the press-coated tablet formulation according to claim 1 to a subject in need thereof, wherein the active agent is a cardiovascular agent.

24. The method according to claim 23 wherein the cardiovascular agent is verapamil.

* * * * *